United States Patent [19]

Scheer

[11] Patent Number: 5,078,492

[45] Date of Patent: Jan. 7, 1992

[54] TEST WAFER FOR AN OPTICAL SCANNER

[75] Inventor: Bradley W. Scheer, Sunnyvale, Calif.

[73] Assignee: VLSI Standards, Inc., Mountain View, Calif.

[21] Appl. No.: 717,879

[22] Filed: Jun. 17, 1991

Related U.S. Application Data

[63] Continuation of Ser. No. 587,334, Sep. 24, 1990, abandoned.

[51] Int. Cl.$^5$ ............................................. G01N 21/88
[52] U.S. Cl. ............................................. 356/243
[58] Field of Search ......................................... 356/243

[56] References Cited

U.S. PATENT DOCUMENTS

| | | | |
|---|---|---|---|
| 4,512,659 | 4/1985 | Galbraith et al. | 356/243 |
| 4,636,073 | 1/1987 | Williams | 356/243 |
| 5,004,340 | 4/1991 | Tullis et al. | 356/243 |

Primary Examiner—Vincent P. McGraw
Attorney, Agent, or Firm—Schneck & McHugh

[57] ABSTRACT

A patterned wafer for testing an optical scanner. The wafer has standard size light scattering features, such as pits, distributed in aligned groups arranged in annular bands about a concentric center. Empty annular bands separate the feature containing annular bands. The empty bands simulate wafer edges for various size wafers. In this manner, wafer edges may be excluded in a particle count for a predetermined size wafer. Apparent size variations in multiple scans indicate misalignments relative to the scan center.

10 Claims, 2 Drawing Sheets

TEST WAFER FOR AN OPTICAL SCANNER

This is a continuation of copending application 07/587,334 filed on Sept. 24, 1990, now abandoned.

TECHNICAL FIELD

The invention relates to testing of optical scanners and in particular to a reference standard for establishing particle counts of a scanner.

BACKGROUND ART

Optical scanners of the type shown in U.S. Pat. No. 4,512,659 to L. Galbraith are used to measure contamination of bare semiconductor wafers before a chip fabrication process begins. Contamination is frequently in the form of particulate matter, with particles ranging in size from very large millimeter size flakes to sub-micron specs of dust or dirt.

In surface scanning, the general state of contamination is an important consideration, but more particularly, the actual particle count is desired information. Most surface scanners scan back and forth in a single direction, while a wafer being inspected is moved beneath the scanning beam in a perpendicular direction. This establishes an x-y scan over a wafer surface. The scan controller usually establishes a wafer-shaped scan pattern so that the scanning beam is always on the wafer surface and does not encounter a wafer edge.

One of the problems encountered in optical surface scanning is that light scattered from a feature on a surface varies depending on the position of the feature relative to the scan center of the beam. There are at least two reasons for such variation. A first reason is that light intensity from the scan center falls off as the square of the distance from that center. Thus a light scattering feature closer to the scan center will present a stronger scattering signal to a remote detector than the same feature further away. A second reason is that the scanning beam spot which falls on the surface varies in cross sectional shape across the surface. A beam which is circular in shape at the center of the surface becomes elliptical at the edge of the surface. Such changes in beam spot shape cause changes in the amount of light scattered from a feature. Additionally, if the scan center is not directly over the center of the surface, there will be an appreciable difference in scattering from opposed edges of the surface. These problems are obviated in telecentric scanners, but many of the surface scanners presently in use are not telecentric.

There is a need for a reference substrate for checking particle count in a surface scanner where beam illumination varies over the surface and where surface edges may be misaligned in relation to the scan center.

SUMMARY OF THE INVENTION

The above need has been met with a reference wafer having groups of light scattering features disposed in spaced-apart, concentric annular bands. Regular groups of light scattering elements are disposed in each annular band and the groups are spaced about each annular band. Groups of same size light scattering features are aligned to come under the scanning beam in the same scan position but in different scans. With this arrangement the scanner should see the same size features in different scans, scattering the same amount of light at the same relative positions.

An operator may size the light scattering features in various groups within a scan line. The variation in size will inform the operator of system errors.

Scattering patterns over a number of scans will let a user know if the scan center is not centered over the wafer. In this situation there will be an appreciable difference in scattering from each edge.

Bands containing light scattering elements are spaced from adjacent similar bands by empty annular bands, allowing for wafer edge simulation and exclusion by a scanner.

BEST MODE FOR CARRYING OUT THE INVENTION

Figure 1:
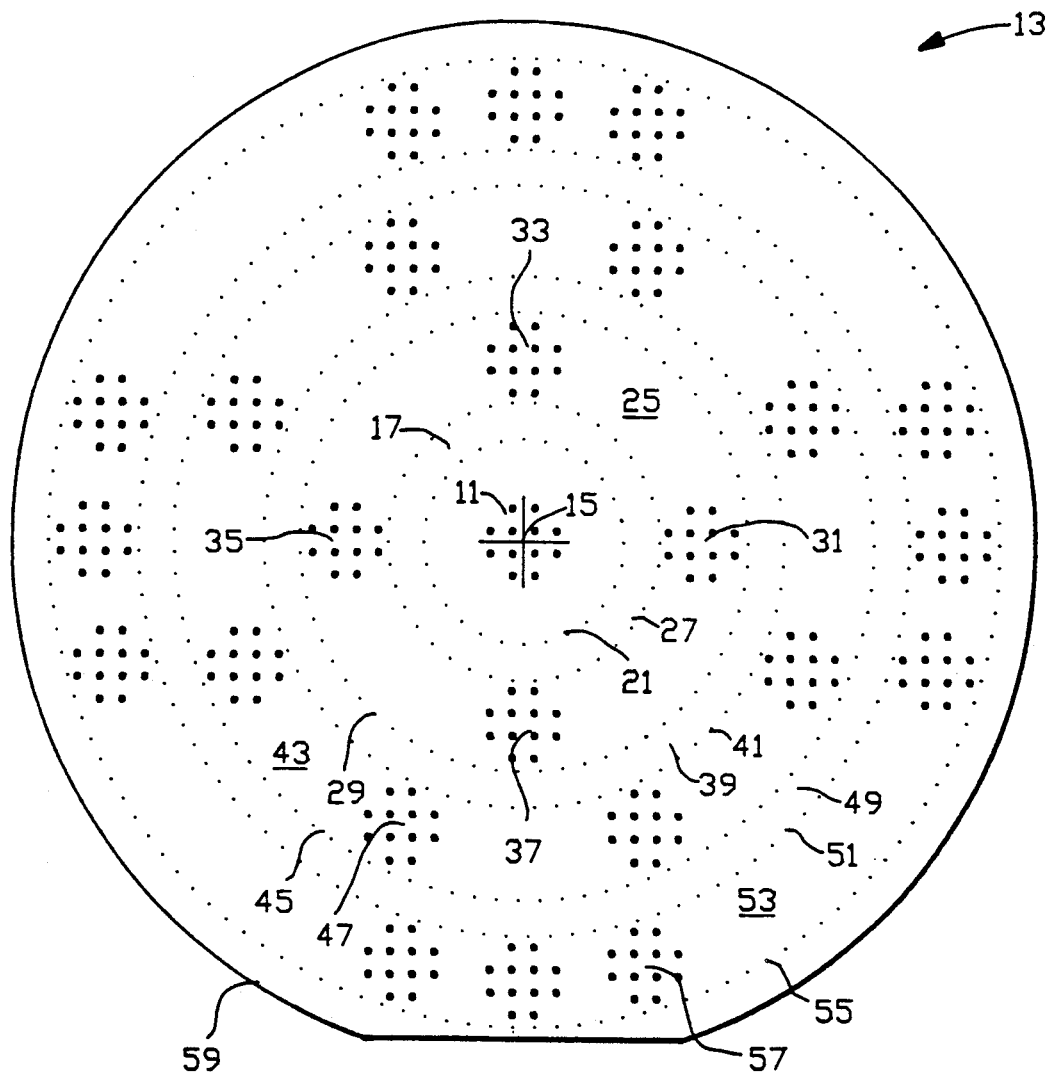
FIG. 1 is a top plan view of a reference standard in accord with the present invention.

With reference to FIG. 1, a wafer having a pattern of light scattering features is shown. The pattern consists of a hierarchical organization of features. At the lowest level, called the group level, there is an array of individual light scattering elements. A first such group 11 is disposed at the geometrical center 15 of the wafer 13. Encircling the first group is an empty annular band 17 having edges indicated by circles 21 and 27. Inner circle 21 is at a radius of about 10 mm from the geometric center 15 while the circle 27 has a 13 mm radius about the center. In this application the cross-hair lines marking the center 15 of the wafer, as well as all of the circular dotted lines indicating annular boundaries, are imaginary lines. The wafer is totally bare except for the patterns of light scattering features.

Next, a first feature containing annular band has inner and outer imaginary band edges 27 and 29, respectively. This first band contains four groups of light scattering features 31, 33, 35 and 37. The distance from the geometric center 15 to the center of a group is 18 mm. The radius of the outer band edge 29 is mm. A second empty annular band 39 is defined between band edge 29 and band edge 41. The radius of band edge 41 is 26 mm.

Next, a second light scattering feature containing band 43 is defined between edges 41 and 45. The radius of edge 45 is 34 mm. Groups of features are disposed within the second band, such as the group 47.

Beyond the second feature containing band 43 is another empty annular band 49 having band edges 45 and 51. The radius of band edge 51 is 38 mm. The empty annular band 49 serves the same purpose as other empty annular bands, allowing edge elimination for scanning over reduced zones. A radius of empty annular bands corresponds to the outer radius of a wafer of predetermined size. The present embodiment assumes a 100 millimeter wafer, but 3 inch and 6 inch wafers, as well as other sizes could also be used. A third and outermost feature containing annular band 53 is defined between band edges 51 and 55. A group of light scattering features 57 is at a radius of 40 mm from the geometric center while the band edge 55 is at a radius of 46 mm. The outer edge 59 of the wafer is at a radius of 50 mm.

The overall distribution of groups on the wafer is one of rows and columns, as well as the previously measured annular distribution, such that at least four groups will be in any row or column. The innermost groups within the first annular band 25 are at a different angular orientation with respect to the center than groups in the second band 43, but the same as the third band 53. By aligning the groups colinearly, light scattering features within different groups of different bands will be seen in the same line scan.

Figure 2:
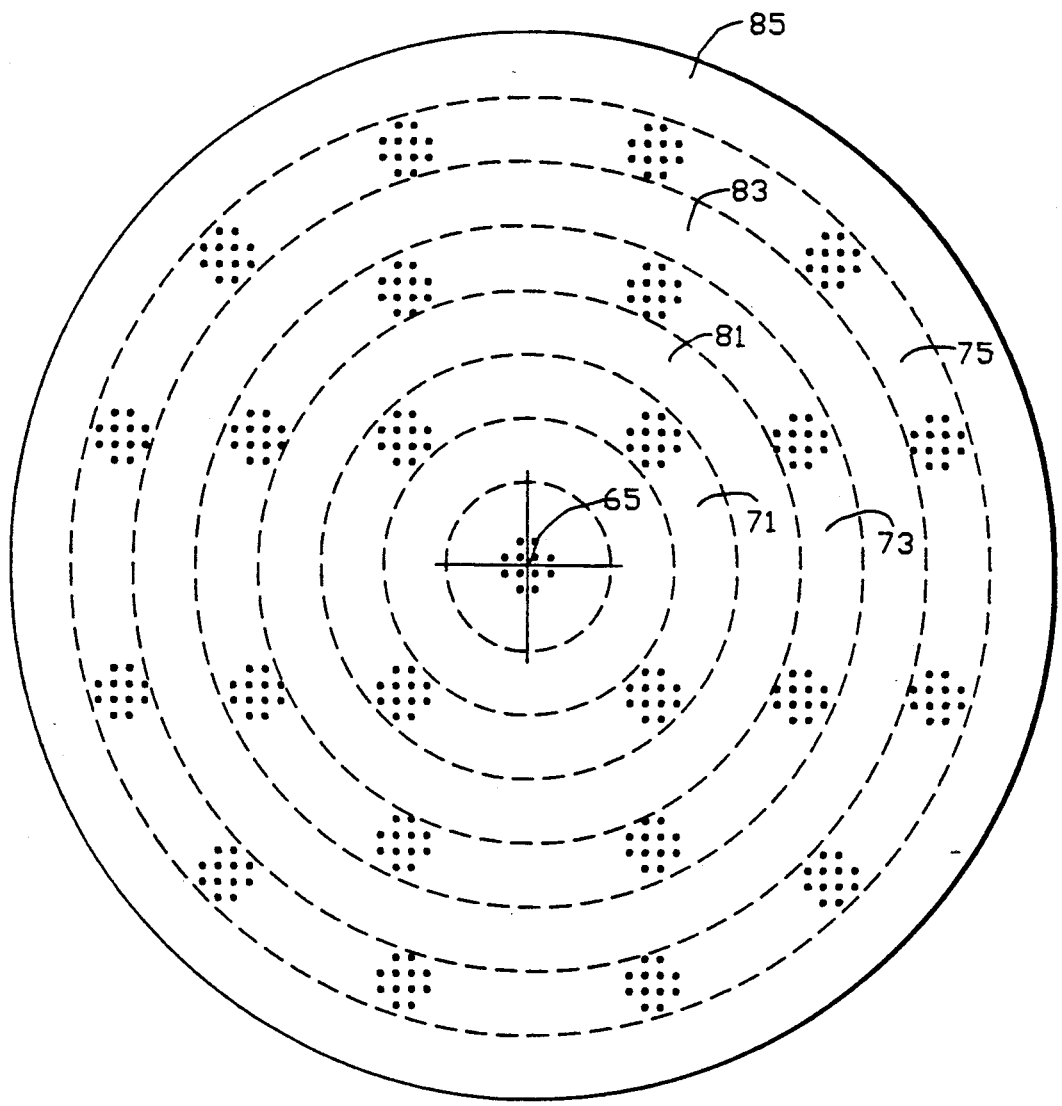
FIG. 2 is a top plan view of another reference standard in accord with the present invention.

With reference to FIG. 2, another pattern of groups of light scattering elements may be seen. Again, the groups are distributed in annular bands about a geometric center 65. Annular bands 71, 73 and 75 which have a common geometric center 65 are spaced apart by empty bands 81, 83 and 85 having the same radial dimensions as the empty bands of FIG. 1. The bands 71, 73 and 75 each contain a plurality of spaced apart groups of light scattering features. The distribution of the groups is once again in rows and columns, with a space between groups greater than twice the width dimension of a group. Since there are twelve light scattering features per group, in the immediate vicinity of the geometric center 65 there will be twelve light scattering elements If the edge exclusion is chosen to be in the first empty annular band 81 so that all groups within annular band 71 are counted, there will be 48 features in the first annular band, plus twelve at the center for a total of 60 light scattering features which should be counted in a scan which includes all light scattering elements within the empty annular band 81. If the annular edge exclusion is pushed outwardly to the second empty annular band 83, there will be an additional eight groups of light scattering elements or a total of 96 which will be scanned. The additional 96 elements give a total of 156 light scattering elements to be scanned.

If the exclusion area is pushed out even further to the third empty annular band 85, then twelve additional groups, lying within annular band 75, will be counted in the total number of groups. The twelve groups in the most outwardly lying band give rise to an additional 144 light scattering elements or a total of 300.

Each of the light scattering features is made by patterning a reflective bare semiconductor wafer. The bare wafer is coated with photoresist and then the coated wafer is patterned with a photomask containing the light scattering elements in a precise pattern. The photomask may be made by a step and repeat camera for uniformity of light scattering elements. Once the wafer is patterned, it may be etched to a desired depth and then all of the photoresist is removed. A typical desired depth is 675 Å. The diameter of an etched pit is 1.5 micrometers. These dimensions are selected so that light scattered from any light scattering feature approximates the amount of light scattered by a 0.269 micrometer latex sphere. Polystyrene latex spheres of these dimensions are provided by the National Institute of Standards and Technology as a standard reference material known as SRM-1691. Other thicknesses will be used to mimic the response from 0.364 micrometer and 0.496 micrometer spheres. Accordingly, an absolute contamination standard may be mimicked by comparing a test wafer with light scattering features made by etching with reference to an absolute standard made by distributing polystyrene latex spheres of the SRM-1691 type.

Figure 3:
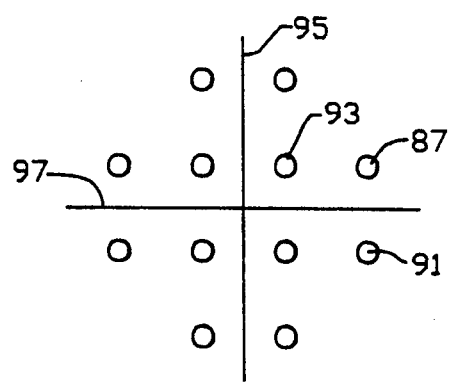
FIG. 3 is a detail of the reference standard of FIG. 1.

Details of the geometry of each light scattering group may be seen with reference to FIG. 3. The spacing between light scattering elements 87 and 91 is 2 mm., but could be in the range of 1 to 3 millimeters. Similarly, the distance between light scattering elements 87 and 93 is also 2 mm. Since the spacing along rows and columns of the array is the same, the dimension across the array is 6 mm. Similarly, the height of the array is 6 mm. The array is symmetric about the x-y axes 95, 97, which are merely imaginary axes and not etched lines. This is also true for the axes seen at the center of FIGS. 1 and 2.

The spacing of light scattering features is such that an illuminating beam spot will illuminate fewer than all of the members of the group. Preferably, only a single spot or a portion of a spot is illuminated at one time. Then, as the beam sweeps across the surface of the wafer, other spots are illuminated and recorded. In this way, a count may be made of the number of spots. If more than one spot is illuminated at one time, counting of spots is more difficult and one must rely upon information gained from repeated passes over the spots.

I claim:

1. A reference for an optical surface scanner comprising,
a wafer having groups of light scattering features disposed in annular bands about the center of the wafer, adjacent bands containing features being spaced apart from each other by empty annular bands, whereby wafer edges may be simulated.

2. The apparatus of claim 1 wherein individual light scattering features in said groups are arranged in a geometric pattern of rows and columns.

3. The apparatus of claim 1 wherein said groups which are in different bands are linearly aligned.

4. A reference for an optical surface scanner comprising,
a wafer having groups of light scattering features distributed radially about a common center, each group having rows and columns of said features of a spacing such that a beam simultaneously illuminates fewer features than in the entire group, said spacing including concentric, empty annular bands simulating wafer edges for various size wafers.

5. The apparatus of claim 4 wherein said light scattering features have a spacing in the range of between 1 and 3 millimeters.

6. The apparatus of claim 4 wherein said light scattering features are pits etched in said wafer surface.

7. The apparatus of claim 4 wherein said light scattering features are disposed in annular bands including a first annular band containing four groups of said features.

8. The apparatus of claim 7 wherein a second annular band contains eight groups of said features.

9. The apparatus of claim 8 wherein a third annular band contains twelve group of said features.

10. The apparatus of claim 4 wherein individual light scattering features in said groups are arranged in a geometric pattern of rows and columns.

* * * * *